US00PP24327P3

(12) United States Plant Patent
Deng et al.

(10) Patent No.: US PP24,327 P3
(45) Date of Patent: Mar. 18, 2014

(54) *CALADIUM* PLANT NAMED 'UF-48-5'

(50) Latin Name: *Caladium×hortulanum*
Varietal Denomination: UF-48-5

(75) Inventors: Zhanao Deng, Riverview, FL (US); Brent K. Harbaugh, Bradenton, FL (US)

(73) Assignee: Florida Foundation Seed Producers, Inc., Marianna, FL (US)

( * ) Notice: Subject to any disclaimer, the term of this patent is extended or adjusted under 35 U.S.C. 154(b) by 114 days.

(21) Appl. No.: 13/506,533

(22) Filed: Apr. 25, 2012

(65) Prior Publication Data

US 2012/0266343 P1 Oct. 18, 2012

(51) Int. Cl.
*A01H 5/00* (2006.01)

(52) U.S. Cl.
USPC ..... Plt./373

(58) Field of Classification Search
USPC ..... Plt./373
See application file for complete search history.

(56) References Cited

U.S. PATENT DOCUMENTS

| | | | |
|---|---|---|---|
| 4,998,277 | A | 3/1991 | Rioux, Jr. |
| 5,624,095 | A | 4/1997 | Zissu |
| 6,648,193 | B2 | 11/2003 | Rioux |
| 7,216,789 | B2 | 5/2007 | Coradimos |
| 7,364,129 | B1 | 4/2008 | Levari, Jr. |
| 2009/0065540 | A1 | 3/2009 | Pantoja |

OTHER PUBLICATIONS

UPOV PLUTO 201303 QZ Citations for 'Ausblanket' Dec. 15, 2011.*

* cited by examiner

*Primary Examiner* — Wendy C Haas
(74) *Attorney, Agent, or Firm* — Jondle Plant Sciences Division of Swanson & Bratschun, L.L.C.

(57) ABSTRACT

A new and distinct cultivar of *caladium* named 'UF-48-5', uniquely characterized by large heart-shaped leaves, a bright pink leaf face, pink veins, and a white background, and demonstrated to produce attractive pot plants when tubers are forced in containers and to produce attractive plants in outdoor shady landscape sites, is disclosed.

4 Drawing Sheets

Genus and species: *Caladium×hortulanum.*
Variety denomination: 'UF-48-5'.

BACKGROUND OF THE NEW PLANT

The present invention relates to a new and distinct cultivar of *caladium* plant, botanically known as *Caladium×hortulanum*, commercially referred to as a strap leaf-type or lance leaf-type and hereinafter referred to by the name 'UF-48-5'.

*Caladiums [Caladium×hortulanum* Birdsey, Araceae Juss.] are ornamental aroids valued for their bright colorful leaves. They are commonly used as container and landscape plants. Pink cultivars have been very popular and the most popular pink cultivars have been 'Carolyn Whorton' (unpatented), 'Fannie Munson' (unpatented), and 'White Queen' (unpatented) (Bell et al., 1998; Deng et al., 2008). They ranked No. 1, No. 3, and No. 4, respectively, in acreage (or popularity) according to a 2003 survey of the *caladium* cultivars commercially grown in Florida, where more than 95% of the *caladium* tubers used in the world are produced (Bell et al., 1998; Deng et al., 2008). Recently, these cultivars have been found rather susceptible to *Pythium* root rot and *Fusarium* tuber rot, the two most important fungal diseases in *caladium* tuber production (Deng et al., 2005; Goktepe et al., 2007). Thus, developing new pink cultivars is an important breeding objective.

This invention relates to a new and distinct cultivar of *caladium* plant named 'UF-48-5'. 'UF-48-5' originated from a cross conducted in 2000 in Bradenton, Fla. between the female parent 'Red Flash' (unpatented) and the male parent 'Candidum Junior' (unpatented). 'Red Flash' was used because of its plant vigor, excellent performance in large containers and landscapes, large tubers, large plants, large leaves, and tolerance to sunburn. 'Candidum Junior' (unpatented) was selected because of its attractive coloration pattern of netted green veins and bright white face and desirable growth habit when grown in containers. A single plant was selected in 2001 for further asexual propagation and evaluation.

'UF-48-5' was first asexually propagated via tubers in 2002 in Bradenton, Fla. Field and pot studies in Bradenton, Fla. between 2001 and 2005 and in Wimauma, Fla. since 2005 have shown that the unique features of 'UF-48-5' are stable and reproduce true to type in successive generations of asexual propagations.

Plant Breeder's Rights for this cultivar have not been applied for. 'UF-48-5' has not been made publicly available more than one year prior to the filing of this application.

SUMMARY OF THE INVENTION

The new *caladium* cultivar 'UF-48-5' has not been observed under all possible environmental conditions. Its phenotype may vary somewhat with variation in the environment such as light intensity and temperature.

The following are the most outstanding and distinguishing characteristics of this new variety when grown under normal horticultural practices in Bradenton, Fla.

1. Large heart-shaped leaves;
2. Unique leaf coloration pattern of a bright pink leaf face, pink veins, and a white background; and
3. Produces attractive plants with improved performance in containers and in outdoor shady landscape sites.

DESCRIPTION OF THE PHOTOGRAPHS

The accompanying photographs illustrate the overall appearance of 'UF-48-5'. The colors shown are as true as can be reasonable obtained by conventional photographic procedures. Colors in the photographs may differ slightly from the color values cited in the detailed botanical description which accurately describe the colors of 'UF-48-5'. The photographs were taken on seven-week-old plants.

DESCRIPTION OF THE NEW VARIETY

Figure 1:
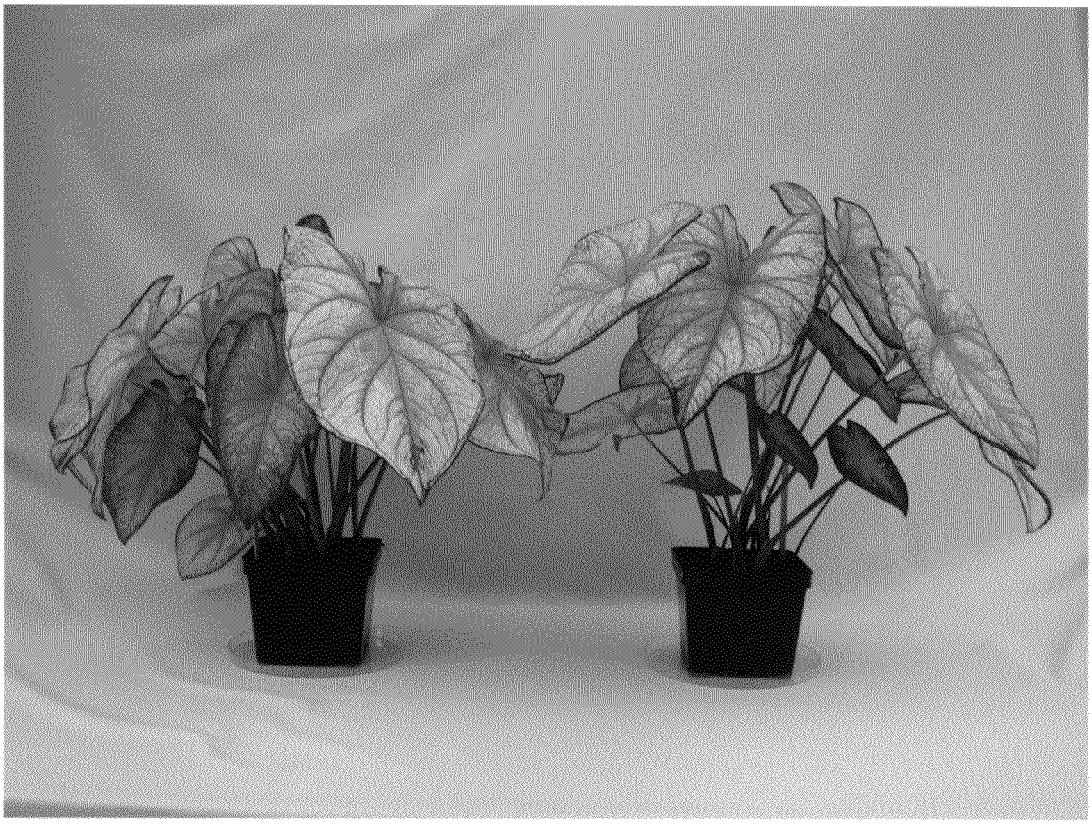
FIG. 1 shows a side perspective view of a typical plant of 'UF-48-5' grown from one de-eyed No. 1 tuber (left) or from one intact (non-de-eyed) tuber in a container in a shadehouse.
Figure 2:
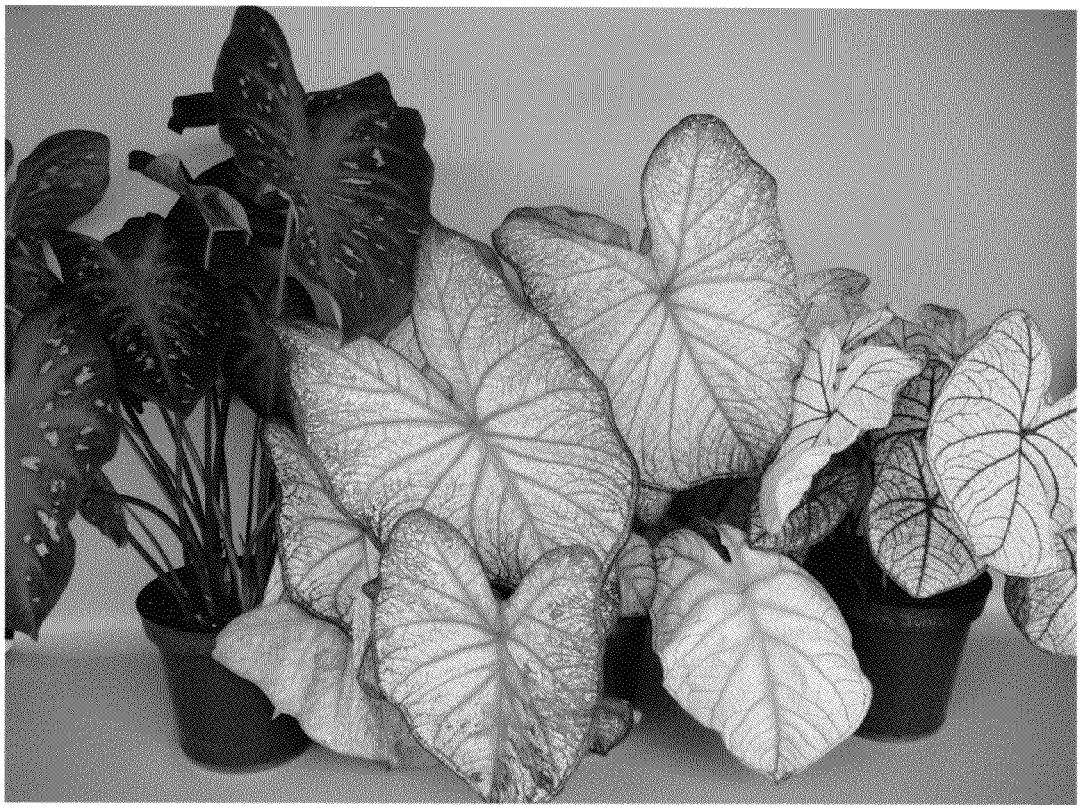
FIG. 2 shows a side perspective view of a typical plant of the seed parent 'Red Flash' (left), 'UF-48-5' (center), and the pollen parent 'Candidum Junior' (right) grown in a shadehouse.
Figure 3:
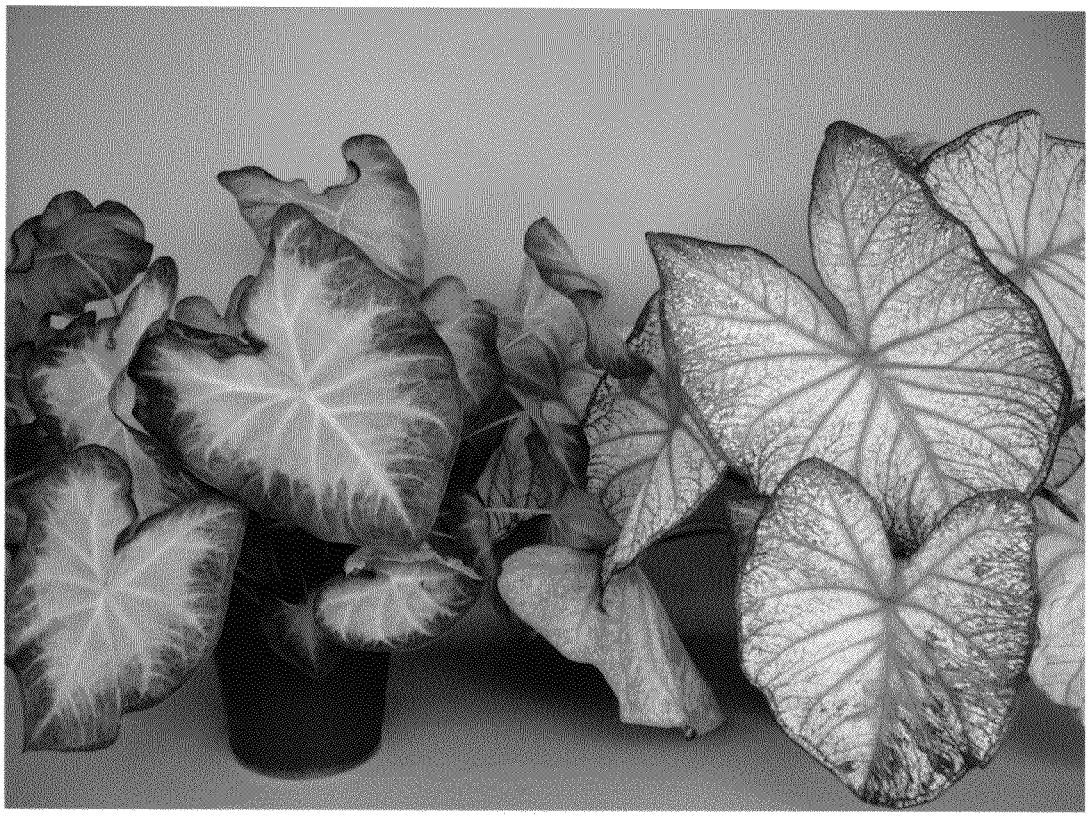
FIG. 3 shows a side perspective view of a typical plant of 'Kathleen' (unpatented; left) and 'UF-48-5' (right) grown in a shadehouse.
Figure 4:
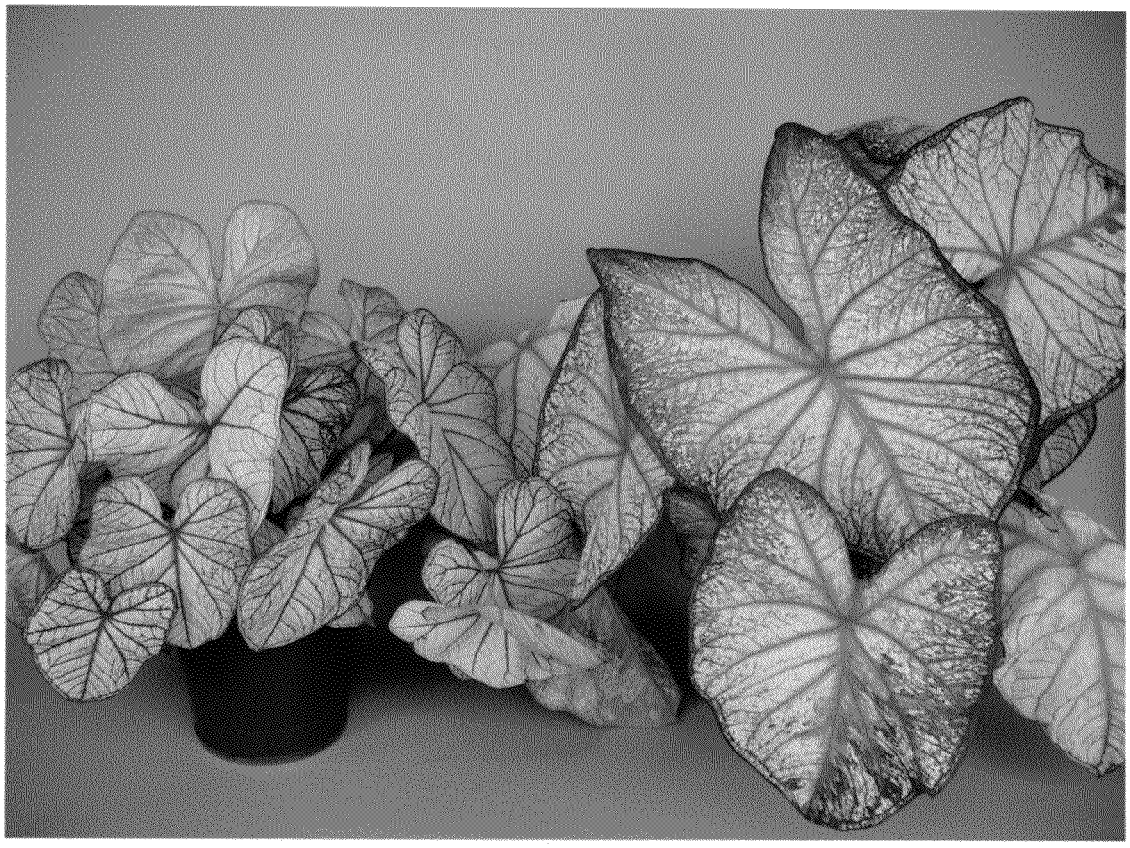
FIG. 4 shows a side perspective view of a typical plant of 'Florida Fantasy' (unpatented; left) and 'UF-48-5' (right) grown in a shadehouse.

The following detailed descriptions set forth the distinctive characteristics of 'UF-48-5'. The data which define these characteristics is based on observations taken in Wimauma, Fla. during the summer of 2011 on plants grown in a polypropylene-covered shadehouse and on plants grown in ground beds in Wimauma, Fla. during the late summer of 2011 in an outdoor nursery. All plants were grown in 20.3 cm containers under conditions and practices which approximate those generally used in commercial *Caladium* production. Plants grown in the shadehouse were about eight weeks from planting tubers when the photographs and the detailed description were taken. Plants grown in the outdoor nursery were about fourteen weeks from planting tuber pieces when the photographs and the detailed description were taken. Color references are made to The Royal Horticultural Society Colour Chart (R.H.S.) (1986 edition), except where general terms of ordinary dictionary significance are used.

DETAILED BOTANICAL DESCRIPTION OF THE NEW PLANT

Classification:

*Family*.—Araceae.

*Botanical*.—*Caladium×hortulanum*.

*Common*.—*Caladium*.

Parentage:

*Female*.—'Red Flash' (unpatented).

*Male*.—'Candidum Junior' (unpatented).

Propagation:

*Type*.—Asexual propagation by tubers and by tuber divisions.

Tuber description:

*Color*.—Epidermis: RHS 200C and RHS 200D (Brown) with areas of RHS 165A (Greyed-orange). Interior: RHS 10C (Yellow) and meristem of RHS 10A (Yellow).

*Time to develop roots and sprout*.—Spring (−15° C. night to 29° C. day): Approximately 2 to 3 weeks Summer (−21° C. night to 35° C. day): Approximately 7 to 10 days.

Root description: Dense, thick and white fleshy roots.

Plant:

*Type*.—Herbaceous perennial.

*Growth habit*.—Semi-upright to spreading; leaf petioles arising from tubers are mostly upright and curve outwardly with development.

*Height* (*shadehouse-grown plants*).—From soil to top of leaf plane: Approximately 31.0 cm to 42.0 cm. From soil to top of inflorescences: Approximately 52.0 cm.

*Height* (*outdoor nursery-grown plants*).—From soil to top of leaf plane: 34.0 cm to 44.0 cm. From soil to top of inflorescences: 43.0 cm.

*Diameter* (*shadehouse-grown plants*).—Approximately 74.0 cm to 64.0 cm.

*Diameter* (*outdoor nursery-grown plants*).—Approximately 57.0 cm to 66.0 cm.

Leaves:

*Size* (*shadehouse-grown plants*).—Length: Approximately 22.0 cm to 34.0 cm. Width (flattened): Approximately 16.0 cm to 27.0 cm.

*Size* (*outdoor nursery-grown plants*).—Length: Approximately 25.0 cm to 30.0 cm. Width (flattened): Approximately 16.0 cm to 17.5 cm.

*Shape*.—Ovate, peltate.

*Apex*.—Acuminate to acute.

*Base*.—Cordate.

*Margin*.—Entire.

*Texture* (*both surfaces*).—Smooth, glabrous.

*Venation pattern*.—Palmate-pinnate.

*Color* (*shadehouse grown plants*).—Developing and fully expanded leaves (upper surface): Center: RHS 54B to RHS 54C (Red) with blotches of RHS 155D (White) and veins of RHS 147A (Yellow-green) and a streak of RHS 53D (Red) from basal notch to sinus. Border and margins: RHS 147A (Yellow-green) with very small blotches of RHS 155D (White). Basal notch: RHS 54A (Red). Venation of midrib and primary veins: RHS 54B (Red) that fades to RHS 183A (Greyed-purple) with bleeding around the veins of RHS 54C (Red). Developing and fully expanded leaves (lower surface): Center: RHS 55A to RHS 55B (Red) with veins of RHS 191A (Greyed-green) and blotches of RHS 155A (White) and a streak of RHS 53C (Red) from basal notch to sinus. Border and margins: RHS 191A (Greyed-green). Venation: Midrib: RHS 36B (Red). Primary: RHS 194A to RHS 194B (Greyed-green). Netted veins: RHS 191A (Greyed-green).

*Color* (*outdoor nursery-grown plants*).—Developing leaves (upper surface): Center: RHS 54A and 54B (Red) with numerous blotches and speckling of RHS 155B (White) and a streak of RHS 53B (Red) from basal notch to sinus. Border and margins: RHS 147A (Yellow-green). Venation: Midrib: RHS 53D (Red). Primary: RHS 53A (Red). Developing leaves (lower surface): Center: RHS 63A and RHS 63C (Red-purple) and blotches of RHS 158B (yellow-white)

and a streak of RHS 53C (Red) from basal notch to sinus. Border and margins: RHS 191A (Greyed-green). Venation: Midrib: RHS 36D (Red). Primary: RHS 157B (Green-white) with a thin center of RHS 194A (Greyed-green). Fully expanded leaves (upper surface): Center: RHS 55B to RHS 55C (Red) with blotches of RHS 158D (Yellow-white) and speckling of RHS 155A (White) with a streak of RHS 53B (Red) from basal notch to sinus. Border and margins: RHS 147A (Green) with speckling of RHS 155A (White). Venation: Midrib: RHS 54B (Red). Primary and secondary veins: RHS 53D (Red). Netted veins: RHS 147A (Green). Fully expanded leaves (lower surface): Center: RHS 63C (Red-purple) with blotches of RHS 158B (Yellow-white) and a streak of RHS 53C (Red) from basal notch to sinus. Border and margins: RHS 191A (Greyed-green). Venation: Midrib: RHS 36D (Red). Primary: RHS 157B (Green-white) with a center of RHS 191B (Greyed-green) and Netted veins: RHS 194A (Greyed-green).

Petiole:

*Aspect*.—Mostly erect, curving outwardly beyond containers.

*Strength*.—Strong; flexible.

*Shadehouse-grown plants*.—Length: Approximately 29.0 cm to 39.0 cm. Diameter (distal): Approximately 5.0 mm. Diameter (proximal): Approximately 9.0 mm. Color: Distal: RHS 182D (Greyed-red). Proximal: RHS 182C (Greyed-red) with streaks of RHS 200B (Brown). Wing: Length: Approximately 4.0 cm to 6.5 cm. Diameter: Approximately 5.0 mm to 7.0 mm. Color: RHS 182C to 182D (Greyed-red) with streaks of RHS 200B (Brown).

*Outdoor nursery-grown plants*.—Length: Approximately 32.0 cm to 40.0 cm. Diameter (distal): Approximately 4.5 mm. Diameter (proximal): Approximately 9.0 mm. Color (proximal): RHS 182D (Greyed-red) with streaks of RHS 200B (Brown). Wing: Length: Approximately 7.0 cm. Diameter: Approximately 7.0 mm. Color: RHS 196D (Greyed-green) with streaks of RHS 200B (Brown).

Inflorescence (data taken only on shadehouse-grown plants):

*Arrangement*.—Upright hooded spathes surrounding a columnar spadix borne on a tall upright scape. Spadix with sessile, simple female and male flowers separated into two zones. Female flowers arranged on the lower one-third of the spadix; male flowers arranged on the upper two-thirds of the spadix. Sterile flowers develop between female and male flower zones; near this area, the spathe constricts surrounding the female flowers.

*Fragrance*.—Absent.

*Natural flowering season/longevity*.—Spring or early summer in central Florida.

*Lastingness of inflorescences*.—Approximately three days before fading; inflorescences persistent.

Spathe:

*Length*.—Approximately 13.0 cm.

*Width (distal)*.—Approximately 5.0 cm.

*Width (proximal)*.—Approximately 2.5 cm.

*Shape*.—Ovate.

*Apex*.—Acute to acuminate.

*Base*.—Tapering.

*Margin*.—Entire.

*Texture*.—Smooth, glabrous.

*Color*.—Upper surface: Upper two-thirds: RHS 155B (White) becoming closer to RHS 199D (Brown) with development. Lower one-third: RHS 143B (Green) with streaks of RHS 145C (Yellow-green). Lower surface: Upper two-thirds: RHS 157B (Green-white). Lower one-third: RHS 144B (Yellow-green) with RHS 187B (Greyed purple) at base.

Spadix:

*Length*.—Entire spadix: Approximately 11.5 cm. Male flower zone: Approximately 7.0 cm. Sterile flower zone: Approximately 1.8 cm. Female flower zone: Approximately 2.7 cm.

*Diameter*.—Male flower zone: Approximately 12.0 mm. Sterile flower zone: Approximately 8.2 mm. Female flower zone: Approximately 11.5 mm.

*Shape*.—Spindle-shaped to columnar.

*Apex*.—Obtuse.

*Base*.—Obtuse.

*Aspect*.—Upright.

*Color*.—Male zone (mature): RHS 158B (Yellow-white). Sterile zone (mature): RHS 158D (Yellow-white). Female zone (mature): RHS 18D (Yellow-orange).

Scape:

*Length*.—Approximately 31.0 cm.

*Diameter*.—Approximately 8.7 mm.

*Strength*.—Sturdy, flexible.

*Aspect*.—Erect.

*Texture*.—Smooth, glabrous; glaucous.

*Color*.—RHS 173D (Greyed-orange) with numerous short streaks of RHS 199A (Grey-brown); just below the spathe, RHS 145B (Yellow-green).

Seed and fruit: None observed.

Disease/pest resistance: Not observed.

COMPARISON OF PARENTAL VARIETY

'UF-48-5' differs from female parent, 'Red Flash' (unpatented), by having leaves with pink veins and a pink leaf face with white background, whereas the leaves of cultivar 'Red Flash' have red veins, a red leaf face with a green background, and pink spots.

'UF-48-5' differs from male parent, 'Candidum Junior' (unpatented), by having leaves with pink veins and a pink leaf face with white background, whereas the leaves of cultivar 'Candidum Junior' have green veins and a white leaf face.

COMPARISON WITH KNOWN CULTIVARS

'UF-48-5' can be compared to plants of the cultivar 'Kathleen' (unpatented). In side-by-side comparisons conducted in a greenhouse in Wimauma, Fla., 'UF-48-5' differs from 'Kathleen' by having a brightly pink-colored leaf center and narrow leaf margins, while 'Kathleen' has a dull pink-colored leaf center and wide, green leaf margins.

'UF-48-5' can also be compared to plants of the cultivar 'Florida Fantasy' (unpatented). In side-by-side comparisons conducted in a greenhouse in Wimauma, Fla., 'UF-48-5' differs from 'Florida Fantasy' in leaf size, leaf coloration pattern, and sunburn tolerance. Leaves of 'UF-48-5' are much larger than those of 'Florida Fantasy', and have a large pink-colored area covering the leaf center, while the red-pink coloration in 'Florida Fantasy' is confined to the main veins. Leaves of 'UF-48-5' are sensitive to sunburns and bleach in color, while leaves of 'Florida Fantasy' are tolerant of sunburns.

'UF-48-5' was evaluated for tuber production and plant performance in Wimauma, Fla. in 2006 and 2007. The soil was an EauGallie fine sand with about 1% organic matter and pH of 6.2. In 2006, raised ground beds (91 cm wide, 20 cm high) were fumigated on 30 March with a mixture of 67% methyl bromide and 33% chloropicrin (by volume) at the rate of 196 $kg \cdot ha^{-1}$ and covered with white-on-black plastic mulch. *Caladium* seed pieces (tuber pieces, ~2.54 cm×~2.54 cm×~2.54 cm) were planted in the beds on 11 April with 15 cm spacing between rows and in rows. A constant water table was maintained below the beds using the seep irrigation system (Geraldson et. al, 1965). Osmocote 18N-2.6P-10K 8-9 month controlled release fertilizer (Scotts Co., Marysville, Ohio) was applied to the bed surface when shoot tips were emerging from the soil with N at 336 $kg \cdot ha^{-1}$. In 2007, the beds (71 cm wide, 21 cm high) were fumigated on 3 April using the same fumigant mixture (196 $kg \cdot ha^{-1}$). *Caladium* seed pieces were planted on 16 April, with 25.4 cm between-row spacing and 15.2 cm in-row spacing. A drip irrigation system was used to provide water (approximately 6 mm per day) and 6N-0.8P-3.9K soluble fertilizer with N at the rate of ~1.9 $kg \cdot ha^{-1} \cdot d^{-1}$ (total N at 290 $kg \cdot ha^{-1}$ per growing season).

Field plots were organized in a randomized complete block design consisting of three replications, and each plot contained 30 propagules. Tubers were dug in December 2006 and January 2008, respectively. Dried tubers were weighed and counted per plot and were then graded by maximum diameter; No. 2 (2.5 to 3.8 cm), No. 1 (3.8 to 6.4 cm), Jumbo (6.4 to 8.9 cm), Mammoth (8.9 to 11.4 cm), and Super Mammoth (>11.4 cm). The production index (PI), an indicator of economic value of the harvested tubers, was calculated as: N (No. 2)+2N (No. 1)+4N (Jumbo)+6N (Mammoth)+8N (Super Mammoth); where N=number of tubers in each grade. An analysis of variance was conducted using the GLM procedure in the SAS program (SAS Institute, 2009) to compare the performance of 'UF-48-5' to that of three commercial pink-leaved cultivars, 'Carolyn Whorton', 'Fannie Munson', and 'White Queen'.

Table 1 shows the weight, weight, production index, number, and grade distribution of five *caladium* cultivars (2006 and 2007). Values presented are means of three replications with 30 propagules planted in a plot.

In 2006, 'UF-48-5' tuber weight was 43% to 71% greater and PI was 31% to 35% higher than those of 'Fannie Munson' and 'White Queen' (Table 1). In 2007, 'UF-48-5', 'Fannie Munson' and 'White Queen' were similar in tuber weight and marketable tuber number. 'UF-48-5' produced larger tubers than 'Fannie Munson' and 'White Queen', more tubers in Mammoth (14.7% vs. 3.0 to 3.3%) and in No. 1 (49.7% vs. 25.3 to 43.3%) in 2006. In 2007, no significant differences in tuber size distribution were observed between 'UF-48-5' and these two comparison cultivars. These data indicate that 'UF-48-5' is as good as, or better than, 'Fannie Munson' and 'White Queen', in tuber production.

Landscape performance under full-sun conditions was evaluated in 2006 and 2007 on the same plots used for evaluating tuber production. The overall plant performance was rated on 2 August and 7 September in the 2006 growing season and on 26 July, 28 August and 25 September in the 2007 growing season, on a scale of 1 to 5, with 1 being very poor (few leaves and lack of vigor), and 5 being excellent (full plants, numerous leaves, and bright color display). At the same time of plant performance evaluation, leaf sun burn tolerance was rated on a scale of 1 to 5, with 1 being very susceptible to sun burns and showing numerous sun-damaged areas or holes on leaves and 5 being resistant to sun burns and not showing any sun-damaged areas. At approximately 4 months after planting, plant height, number of leaves, and foliar characteristics were measured.

TABLE 1

| Cultivar | Tuber Weight (kg) | Tuber Production index | Tuber Marketable (No.) |
|---|---|---|---|
| | Year 2006 | | |
| 'UF-48-5' | 5.3 a | 173 a | 59.0$^{NS}$ |
| 'Carolyn Whorton' | 6.0 a | 169 a | 62.1 |
| 'Fannie Munson' | 3.1 b | 132 b | 54.5 |
| 'White Queen' | 3.7 b | 128 b | 47.1 |
| | Year 2007 | | |
| 'UF-48-5' | 4.4$^{NS}$ | 117$^{NS}$ | 38.2$^{NS}$ |
| 'Carolyn Whorton' | 4.6 | 123 | 46.3 |
| 'Fannie Munson' | 3.8 | 108 | 42.0 |
| 'White Queen' | 4.7 | 166 | 50.9 |

| Cultivar | Tuber distribution (%)[z] Super mammoth | Mammoth | Jumbo | No. 1 | No. 2 |
|---|---|---|---|---|---|
| | Year 2006 | | | | |
| 'UF-48-5' | 0$^{NS}$ | 14.7 a | 25.7 b | 49.7 a | 9.7 b |
| 'Carolyn Whorton' | 2.0 | 18.7 a | 17.7 b | 17.3 c | 44.7 a |
| 'Fannie Munson' | 0 | 3.0 b | 27.7 b | 43.3 b | 25.3 ab |
| 'White Queen' | 0 | 3.3 b | 46.3 a | 25.3 c | 25.3 ab |
| | Year 2007 | | | | |
| 'UF-48-5' | 1.0$^{NS}$ | 15.0$^{NS}$ | 30.0 ab | 38.7 ab | 15.7 b |
| 'Carolyn Whorton' | 1.0 | 10.0 | 31.7 ab | 23.3 b | 34.0 a |
| 'Fannie Munson' | 0.7 | 8.3 | 18.0 b | 54.7 a | 18.7 ab |
| 'White Queen' | 0.7 | 12.3 | 42.0 a | 34.0 ab | 11.3 b |

[z]Tubers graded by maximum diameter; No. 2 (2.5 to 3.8 cm), No. 1 (3.8 to 6.4 cm), Jumbo (6.4 to 8.9 cm), Mammoth (8.9 to 11.4 cm), and Super Mammoth (>11.4 m). Tuber distribution data (%) were transformed using the formula arcsine [square root (percentage/100)] before analysis of variance and mean separation.
[y]The production index is an indicator of economic value of the crop harvested and is calculated as: N (No. 2) + 2N (No. 1) + 4N (Jumbo) + 6N (Mammoth) + 8N (Super Mammoth), where N = number of tubers in each grade.
[x]Mean separation within column by Fisher's least-significant-difference test at $P \leq 0.05$.
[NS]Not significantly different within column by F test at $P = 0.05$.

Table 2 shows plant characteristics, performance, and sunburn tolerance from planting 2.54 cm *caladium* tuber propagules in ground beds in full sun (2006 and 2007). Values presented for plant height, leaf number, length and width are means of three replications with three plants measured per plot per year, while performance and sun burn tolerance ratings are means of three replications based on whole plot evaluation.

'UF-48-5' was similar to 'Carolyn Whorton' in plant height (~37 cm tall), leaf number (18 to 21), leaf length (27 to 29 cm), and leaf width (17 to 18 cm), but 'UF-48-5' was significantly taller than 'Fannie Munson' and 'White Queen' in plant height (Table 2). 'UF-48-5' produced significantly more leaves than 'White Queen' and its leaves were 2 to 5 longer than those of 'Fannie Munson' or 'White Queen'. Plant performance ratings of 'UF-48-5' were comparable to those of 'Carolyn Whorton' in both 2006 and 2007 growing seasons. 'UF-48-5' performed better than 'Fannie Munson' in both years and also better than 'White Queen' in 2006. In full sun, leaves of 'UF-48-5' did not show any leaf tissue damages from sunburns (holes or "windows" on leaf blades), but did bleach out and fade into light pink, especially in July and August when sun light levels and air temperatures in Florida were high. As a result, 'UF-48-5' received lower sunburn tolerance ratings than 'Carolyn Whorton' and 'White Queen' (Table 2). This indicates that 'UF-48-5' is more suited for partially shady locations in landscape use.

TABLE 2

| Cultivar | Plant height[z] (cm) | Leaf number[z] (no.) | Length[z] (cm) | Width[z] (cm) |
|---|---|---|---|---|
| 'UF-48-5' | 36.7 a | 18.8 ab | 28.5 a | 17.7 |
| 'Carolyn Whorton' | 36.5 a | 20.6 a | 27.0 ab | 17.6 |
| 'Fannie Munson' | 27.6 b | 15.7 bc | 26.1 b | 17.0 |
| 'White Queen' | 28.1 b | 13.7 c | 24.9 b | 17.8 |

| | Performance rating[y] | | | | |
|---|---|---|---|---|---|
| Cultivar | August 2006 | September 2006 | July 2007 | August 2007 | September 2007 |
| 'UF-48-5' | 2.7 a | 3.8 a | 3.1 a | 3.7 a | 4.4 |
| 'Carolyn Whorton' | 2.2 ab | 3.2 a | 3.1 a | 3.7 a | 4.5 |
| 'Fannie Munson' | 1.7 bc | 2.5 b | 2.1 b | 2.7 b | 3.5 |
| 'White Queen' | 1.0 c | 1.2 c | 3.3 a | 3.5 a | 3.6 |

| | Sun tolerance rating[x] | | | | |
|---|---|---|---|---|---|
| Cultivar | August 2006 | September 2006 | July 2007 | August 2007 | September 2007 |
| 'UF-48-5' | 3.0 c | 3.9 b | 1.8 c | 2.4 d | 3.9 c |
| 'Carolyn Whorton' | 3.8 ab | 4.2 ab | 3.6 ab | 4.3 b | 4.3 b |
| 'Fannie Munson' | 3.3 bc | 4.1 ab | 3.3 b | 3.9 c | 4.0 c |
| 'White Queen' | 3.8 ab | 4.3 a | 3.5 b | 4.8 a | 4.6 a |

[z]Data were taken over two growing seasons (2006 and 2007), approximately 4 months (August 2006 and 2007) after tubers were planted in April each year.
[y]Plants were rated on a scale of 1 to 5, with 1 being very poor, 3 fair and acceptable, and 5 being excellent in plant vigor, fullness, and color display.
[x]Plants' sun burn tolerance was rated on a scale of 1 to 5, with 1 being very poor, 3 fair and acceptable, and 5 being excellent without showing any signs of leaf burns or resulted holes on leaf surfaces.
[w]Mean separation within columns by Fisher's least-significant-difference test at $P \leq 0.05$.

Table 3 shows plant performance for *caladium* cultivars grown from No. 1 tubers in 11.4 cm containers in a 45% shaded glasshouse, 2007, Wimauma, Fla. Values represent the means of 10 plants produced from intact or de-eyed No. 1 (3.8 to 6.4 cm in diameter) tubers planted individually per container. Data were taken 8 weeks after planting.

The suitability of 'UF-48-5' for container forcing was evaluated by forcing tubers in 11.4 cm containers and comparing them to forced plants of 'Kathleen' *caladium*. No. 1 tubers were planted either intact or de-eyed in a peat/vermiculite mix (VerGro Container Mix A, Verlite, Tampa, Fla.) on 26 Mar. 2007. The study was conducted in a greenhouse with 45% light exclusion during the summer in Wimauma, Fla. Average daily temperatures ranged from a low of 16° C. night to 29° C. day during the experiment. Potted plants were arranged on metal benches in the greenhouse in a randomized complete block design with 10 replications. Plant height, number of leaves, and foliar characteristics were recorded 8 weeks after planting.

When intact tubers were planted, 'UF-48-5' sprouted in about 31 days, nearly 6 days later than 'Kathleen'. De-eyed tubers of 'UF-48-5' sprouted 13 days later than those of 'Kathleen' (Table 3). Plants from intact 'UF-48-5' tubers were taller, had less leaves but larger leaves, than 'Kathleen', resulting in lower plant quality ratings for plants produced in small pots. De-eyed plants of these cultivars were similar in height, but leaf number was less and leaf size larger for 'UF-48-5' compared to 'Kathleen'. However, plant quality ratings were higher for 'UF-48-5' than 'Kathleen' due to the striking color and leaf display of 'UF-48-5'. Overall, tuber de-eyeing improved 'UF-48-5' plant quality considerably.

TABLE 3

| | Days to sprout[z] | | Plant height (cm) | |
|---|---|---|---|---|
| Cultivar | Intact | De-eye | Intact | De-eye |
| 'UF-48-5' | 31.4 a | 35.8 a | 31.6 a | 27.7 |
| 'Kathleen' | 25.7 b | 22.8 b | 24.1 b | 23.5 |

| | Leaves (no.) | | Leaf length (cm) | |
|---|---|---|---|---|
| Cultivar | Intact | De-eye | Intact | De-eye |
| 'UF-48-5' | 6.1 b | 12.3 b | 33.9 a | 23.3 a |
| 'Kathleen' | 13.9 a | 20.0 a | 19.0 c | 14.9 b |

| | Leaf width (cm) | | Quality rating | |
|---|---|---|---|---|
| Cultivar | Intact | De-eye | Intact | De-eye |
| 'UF-48-5' | 23.7 a | 15.0 a | 2.4 b | 4.4 a |
| 'Kathleen' | 12.0 b | 8.7 b | 3.2 a | 3.6 b |

[z]Number of days from planting to the first unfurled leaf. Mean separation within column by Fisher's least-significant-difference test at $P \leq 0.05$.

We claim:

1. A new and distinct variety of *caladium* plant named 'UF-48-5' as shown and described herein.

* * * * *

UNITED STATES PATENT AND TRADEMARK OFFICE

CERTIFICATE OF CORRECTION

PATENT NO. : PP24,327 P3
APPLICATION NO. : 13/506533
DATED : March 18, 2014
INVENTOR(S) : Zhanao Deng and Brent K. Harbaugh It is certified that error appears in the above-identified patent and that said Letters Patent is hereby corrected as shown below:

In the Specification

1. Column 1, Lines 8-9: “strap leaf-type or lance leaf-type” should read -- “fancy leaf-type” --.

2. Column 4, Lines 4-5: Remove -- “and meristern of RHS 10A (Yellow)” --.

3. Column 4, Line 6: Remove the (-) symbol from “-15° C”.

4. Column 4, Line 8: Remove the (-) symbol from “-21° C”.

Signed and Sealed this
Twenty-fourth Day of June, 2014

Michelle K. Lee

Michelle K. Lee
*Deputy Director of the United States Patent and Trademark Office*